United States Patent [19]

Ohki et al.

[11] Patent Number: 5,989,217
[45] Date of Patent: *Nov. 23, 1999

[54] MEDICINE ADMINISTERING DEVICE FOR NASAL CAVITIES

[75] Inventors: Hisatomo Ohki; Shigemi Nakamura; Kazunori Ishizeki; Yoshiyuki Yazawa, all of Gunma; Akira Yanagawa, Yokohama, all of Japan

[73] Assignees: Unisia Jecs Corporation, Atsugi; Dott Limited Company, Yokohama, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/823,314

[22] Filed: Mar. 21, 1997

[30] Foreign Application Priority Data

Mar. 21, 1996 [JP] Japan .................................. 8-092023

[51] Int. Cl.$^6$ .................................................. A61M 11/00
[52] U.S. Cl. ................. 604/94; 128/200.22; 128/203.21; 604/244
[58] Field of Search ................................. 604/54, 57, 58, 604/94, 516, 244; 128/200.22–200.23, 203.21–203.23, 204.11–204.12

[56] References Cited

U.S. PATENT DOCUMENTS

| | | | |
|---|---|---|---|
| 1,105,934 | 8/1914 | Stevens . | |
| 1,442,253 | 1/1923 | Cooper . | |
| 2,470,297 | 5/1949 | Fields | 604/94 |
| 3,502,078 | 3/1970 | Hill et al. | 128/232 |
| 4,889,114 | 12/1989 | Kadders | 604/58 |
| 5,284,132 | 2/1994 | Geier | 604/94 |
| 5,619,985 | 4/1997 | Ohki et al. | 128/203.21 |
| 5,647,349 | 7/1997 | Ohki et al. | 128/203.15 |
| 5,715,811 | 2/1998 | Ohki et al. | 128/203.21 |

FOREIGN PATENT DOCUMENTS

| | | |
|---|---|---|
| 203 358 | 10/1908 | Germany . |
| 40 37 783 A1 | 9/1991 | Germany . |
| 97-701572 | 4/1997 | Rep. of Korea . |
| 898649 | 6/1962 | United Kingdom ...................... 604/58 |
| 1436028 | 5/1973 | United Kingdom ...................... 604/58 |
| 1338254 | 11/1973 | United Kingdom ...................... 604/58 |
| WO 92/21404 | 12/1992 | WIPO . |
| 9311818 | 6/1993 | WIPO ..................................... 604/58 |

*Primary Examiner*—Mark Bockelman
*Attorney, Agent, or Firm*—Foley & Lardner

[57] ABSTRACT

A medicine administering device for nasal cavities, comprising a capsule holding section formed with a capsule containing powder-state medicine. An air supply section is connected to the lower end of the capsule holding section and formed with an air supply passage which is in communication with the capsule accommodating chamber. A branched passage section is connected to the upper end of the capsule holding section and has an air flow passage in communication with the capsule accommodating chamber. The air flow passage is bifurcated to form first and second outlet passage portions which are arranged to form a generally Y-shape. First and second medicine passages are formed such that air from the branched passage section flows therethrough to carry the medicine in the capsule into right-side and left-side nasal cavities of a patient. The first and second passages are respectively in communication with the first and second outlet passages of the branched passage section. First and second spraying holes are respectively in communication with the first and second medicine passages, the medicine from the first medicine passage and the medicine from the second medicine passage being sprayed respectively from the first and second spraying holes. The first and second spraying holes respectively have first and second axes which are separate from each other by a distance ranging from 12 to 25 mm.

9 Claims, 5 Drawing Sheets

MEDICINE ADMINISTERING DEVICE FOR NASAL CAVITIES

BACKGROUND OF THE INVENTION

1. Field of the Invention

This invention relates to improvements in a medicine administering device suitable for administering, for example, powder-state medicine into right-side and left-side nasal cavities of a patient.

2. Description of the Prior Art

In general, a method of curing by administering powder-state medicine through nasal cavities can be employed for a patient with nasal allergy, asthma or the like. In this curing method, an exclusive sprayer or medicine administering device is usually used in which a capsule filled with powder-state medicine is accommodated in a medicine accommodating chamber. The powder-state medicine inside the capsule is administered into the nasal cavities of the patient. An example of such a sprayer to be used for this curing method is disclosed in Japanese Patent Provisional Publication No. 59-34267.

This conventional sprayer includes a cylindrical body member which is formed with a capsule accommodating chamber in which a capsule containing powder-state medicine is accommodated. An air supply passage connects to the capsule accommodating chamber. The cylindrical body member is formed at its tip end portion with a medicine spraying hole through which the medicine in the capsule is sprayed into one of the nasal cavities of the patient. The medicine spraying hole is in communication with the capsule accommodating chamber. The capsule in the capsule accommodating chamber is perforated by a needle to be inserted through the medicine spraying hole.

With such a conventional sprayer, an operation for administering the powder-state medicine to the patient has been carried out as follows: First, the tip end portion (formed with the medicine spraying hole) of the cylindrical body member is inserted into one of the nasal cavities of the patient. Then, air is forced through the air supply passage into the capsule which has been perforated, so that the medicine in the capsule is carried through the medicine spraying hole into the nasal cavities of the patient. This operation is repeated alternately for the right-side and left-side nasal cavities of the patient in order to complete a medicine administration to the patient.

However, drawbacks have been encountered in the above conventional sprayer, in which administering the medicine to the patient is accomplished by alternately and repeatedly inserting the tip end section of the cylindrical body member into the right-side and left-side nasal cavities, and therefore it is difficult to supply the right-side and left-side nasal cavities with equal amounts of the medicine. This makes the medicine administering operation troublesome and requires a considerable time for the medicine administering operation.

SUMMARY OF THE INVENTION

It is an object of the present invention to provide an improved medicine administering device for nasal cavities, which can effectively overcome drawbacks encountered in conventional sprayers or medicine administering devices for nasal cavities.

Another object of the present invention is to provide an improved medicine administering device for nasal cavities, which can largely facilitate an operation for administering powder-state medicine into the nasal cavities of a patient, while making it possible to administer the powder-state medicine to a variety of persons including children and adults.

A first aspect of the present invention resides in a medicine administering device for nasal cavities, comprising a capsule holding section for holding a capsule containing powder-state medicine. An air supply section is provided to supply air toward the capsule held in the capsule holding section, the air supply section being connected to the capsule holding section. First and second medicine passages are formed such that air from the air supply section flows therethrough to carry the medicine in the capsule into right-side and left-side nasal cavities of a patient. First and second spraying holes are formed to be respectively in communication with the first and second medicine passages. The medicine from the first medicine passage and the medicine from the second medicine passage are sprayed respectively from the first and second spraying holes. The first and second spraying holes respectively have first and second axes which are separate from each other by a distance ranging from 12 to 25 mm.

A second aspect of the present invention resides in a medicine administering device for nasal cavities, comprising a capsule holding section including means defining a capsule accommodating chamber for accommodating a capsule containing powder-state medicine. An air supply section is provided to supply air toward the capsule held in the capsule holding section, the air supply section being connected to a first end of the capsule holding section and formed with an air supply passage which is in communication with the capsule accommodating chamber. A branched passage section is provided such that an air flow passage in communication with the capsule accommodating chamber is bifurcated at the branched passage section to form first and second outlet passage portions. The air flow passage and the first and second outlet passage portions are arranged to form a generally Y-shape. The branched passage section is connected to a second end of the capsule holding section. First and second medicine passages are formed such that air from the branched passage section flows therethrough to carry the medicine in the capsule into right-side and left-side nasal cavities of a patient. The first and second passages are respectively in communication with the first and second outlet passages of the branched passage section. First and second spraying holes are respectively in communication with the first and second medicine passages, the medicine from the first medicine passage and the medicine from the second medicine passage being sprayed respectively from the first and second spraying holes. The first and second spraying holes respectively have first and second axes which are separate from each other by a distance ranging from 12 to 25 mm.

A third aspect of the present invention resides in a medicine administering device for nasal cavities, comprising first and second medicine passages which are to be in communication with right-side and left-side nasal cavities of a patient. First and second capsule accommodating chambers are formed to accommodate respectively first and second capsules, each containing powder-state medicine. The first and second capsule accommodating chambers are respectively in communication with the first and second medicine passages so that the medicine in the first capsule and the medicine in the second capsule are supplied respectively into the first and second medicine passages. An air supply section is formed with an air supply passage through which air flow is to be supplied. A branched passage section is provided such that an air flow passage in communication with the air supply passage is bifurcated at the branched passage section to form first and second outlet passage portions which are respectively in communication with the first and second capsule accommodating chambers, the air flow passage and the first and second outlet passage portions generally forming a Y-shape. The branched passage section is disposed between the first and second capsule accommodating chambers defining means and the air supply section. First and second spraying holes are formed to be respectively in communication with the first and second medicine passages. The medicine from the first medicine passage and the medicine from the second medicine passage are sprayed respectively from the first and second spraying holes. The first and second spraying holes respectively have first and second axes which are separate from each other by a distance ranging from 12 to 25 mm.

According to the above aspects of the present invention, during administration of the power-state medicine to the patient, air is supplied to the capsule from the air supply section and directed into the capsule to form an air stream containing the medicine. Then, the air stream containing the medicine is passed through the right-side and left-side medicine passages and sprayed from the right-side and left-side spraying holes of nozzle portions into the right-side and left-side nasal cavities of the patient. Thus, both the nasal cavities of the patient can be simultaneously supplied with the medicine, thereby omitting repetition of inserting a sprayer alternately into the right-side and left-side nasal cavities of the patient and administering the medicine to each nasal cavity many times like with conventional medicine administering devices. This largely facilitates the medicine administering operation, while shortening the time required for the medicine administering operation. Additionally, the centers (axes) of the respective spraying holes of the nozzle portions are set within a range of 12 to 25 mm, and therefore the spraying holes can be securely positioned respectively in the nasal cavities of a variety of patients, including children who have a relatively small distance between nasal cavities and adults who have a relatively large distance between nasal cavities. This makes it possible to administer the medicine to a required position in each nasal cavity while improving the effects of the medicine.

DETAILED DESCRIPTION OF THE INVENTION

Figure 1:
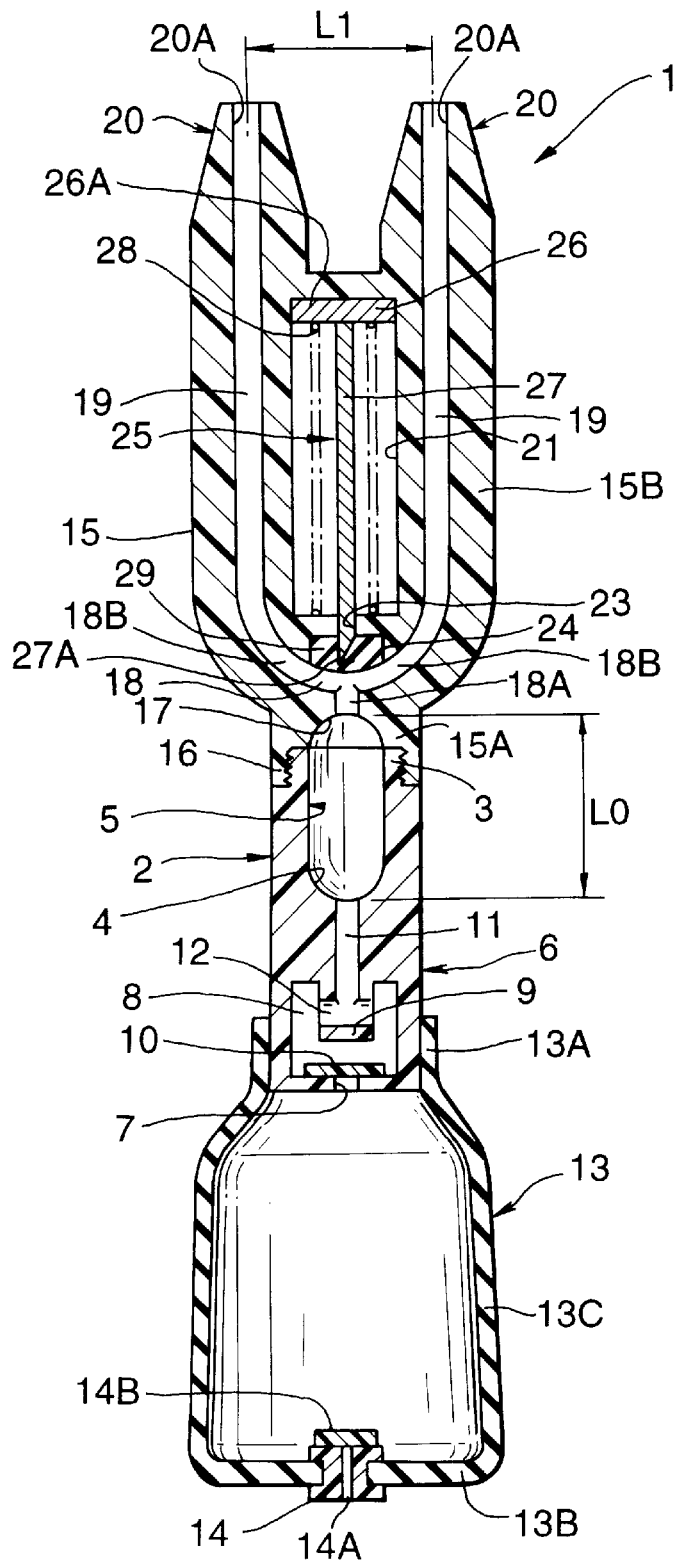
FIG. 1 is a vertical cross-sectional view of a first embodiment of a medicine administering device for nasal cavities, according to the present invention, showing a first operational state of the device.

Referring now to FIGS. 1 to 4, a first embodiment of a medicine administering device for nasal cavities is illustrated by the reference numeral 1. The medicine administering device 1 generally comprises a capsule holder 2 which is formed of plastic and formed into a cylindrical column-like shape. The upper end section of the capsule holder 2 is formed at its outer peripheral surface with an external thread 3. The capsule holder 2 is formed with a capsule hole lower part 4 which extends axially and opens at the upper end face of the capsule holder 2. The capsule hole lower part 4 is coaxial with the capsule holder 2. The capsule hole lower part 4 is adapted to be combined with a capsule hole upper part 17, which will be discussed below, to form a capsule accommodating chamber 5.

The capsule accommodating chamber 5 is adapted to accommodate therein a generally cylindrical capsule K (shown in FIG. 2) which has a volume ranging from 0.1 to 1.4 cc, preferably 0.2 to 0.6 cc. The capsule K is filled with a suitable amount of powder-state medicine (referred hereinafter as "medicine powder"). Additionally, the capsule accommodating chamber 5 is set such that the axial dimension LO thereof is slightly smaller than the axial dimension LK of the capsule K so that the capsule K is accommodated in the capsule accommodating chamber 5 in an axially, securely supported state.

An air supply section 6 is formed integral at its upper end section with the capsule holder 2 and coaxially extends from the capsule holder 2. The air supply section 6 is formed at its lower end section with an air supply valve chamber 8, which communicates with a pump 13 (discussed below) through an air flow passage 7. A valve opening amount restricting portion 9 is formed in the air supply valve chamber 8 in a manner to be projected downward from the side of the capsule holder 2 and extends toward the air supply passage 7. An air supply valve member 10 is disposed within the air supply valve chamber 8 and located facing and spaced from the valve opening amount restricting portion 9. The air supply valve member 10 is located on the air flow passage 7 and adapted to move upward to come into contact with the valve opening amount restricting portion 9 so as to open the air flow passage 7 when air is supplied from the pump 13, and adapted to be seated on a bottom wall of the air supply section 6 to close the air supply passage 7. The air supply section 6 is formed at its upper section with an air supply passage 11 which is located at the central portion thereof and extends axially. The lower end of the air supply passage 11 is in communication with a medicine powder receiving portion or laterally extending hole 12 which is formed piercing the valve opening amount restricting portion 9 to extend in a diametrical direction of the air supply section 6. The medicine powder receiving portion 12 is adapted to receive medicine powder dropped from the capsule K to the side of the air supply valve member 10 when a through-hole H is formed in the capsule K by a pin 27 which is discussed below (See FIG. 3).

The upper end of the air supply passage 11 is in communication with the bottom of the capsule hole lower part 4. The air supply passage 11 has a cross-sectional area ranging from 0.2 to 6.0 $mm^2$, preferably 1.0 to 4.5 $mm^2$, so that air to be supplied from the pump 13 is supplied into the capsule K at a suitable amount and at a suitable flow speed so as to mix the medicine powder in the capsule K with air at a good mixing ratio. The cross-sectional area of the air supply passage 11 is set to prevent the air supply passage 11 from being clogged with the medicine powder or the like.

The pump 13 is of the manually operated type and formed of a flexible material, such as rubber or plastic, and is formed into the shape of bellows. The pump 13 is formed into a generally cylindrical shape having a closed bottom so as to include a generally cylindrical mouth portion 13A, a circular bottom portion 13B and a generally cylindrical pressable portion 13C. The mouth portion 13A is integral with the upper end of the pressable portion 13C, while the bottom portion 13B is integral with the lower end of the pressable portion 13C. The mouth portion 13A is fitted on the outer peripheral surface of the air supply section 6 to maintain an airtight seal. The pump 13 is set to discharge air in an amount (referred to as "air discharge amount") ranging from 10 to 60 cc, and preferably 20 to 40 cc, by one pressing action of the pressable portion 13C, for example, by fingers of the patient in a manner to discharge a generally whole amount of air inside the pump 13, thereby supplying a suitable amount of air to the capsule K through the air supply section 6. In other words, the volume of air contained in the pump 13 may be within a range of 10 to 60 cc, preferably 20 to 40 cc.

A suction valve 14 is disposed at the central part of the bottom portion 13B and includes a valve member 14B which is adapted to open or close an air suction passage 14A. The air suction passage 14A is formed in a valve body (no numeral) securely fitted to the wall of the bottom section 13B. The valve member 14B is arranged to close the air suction passage 14A when air is supplied therefrom to the capsule K, and to open the air suction passage 14A when air is sucked toward the pump 13.

A passage member 15 is connected to the upper end section of the capsule holder 2 and formed of plastic. The lower end section (or the axially one end) of the passage member 15 is formed in a generally cylindrical shape at its outer peripheral surface and has a small outer diameter which is the same as that of the upper section of the capsule holder 2. The upper section (having the axially other end) of the passage member 15 is formed in a generally cylindrical shape at its outer peripheral surface and has a large outer diameter which is larger than that of the lower end section. Thus, the passage member 15 is formed into a column-like shape having an annular step. The lower end section of the passage member 15 is formed at its inner peripheral surface with an internal thread 16 which is to be engaged with the external thread 3 of the capsule holder 2. Additionally, the lower end section of the passage member 15 is coaxially formed with the capsule hole upper part 17, which is opened at its one end so as to be combined with the capsule hole lower part 4 of the capsule holder 2, thereby forming the capsule accommodating chamber 5.

The passage member 15 includes a branched passage section 18 which has an inlet passage portion 18A which extends axially and is in communication with the capsule accommodating chamber 5 (more specifically to the capsule hole upper part 17). The branched passage section 18 further has right-side and left-side outlet passage portions 18B, 18B which bifurcate from the inlet passage portion 18A so as to be in communication with the inlet passage portion 18A. Each outlet passage portion 18B is formed curved and extends upwardly to be arcuate. Thus, the passage portions 18A, 18B, 18B of the branched passage section 18 are arranged in a generally Y-shape. The upper ends of the outlet passage portions 18B, 18B are connected respectively with medicine powder passages 19, 19 formed in the passage member 15. The branched passage section 18 functions to separately direct air containing medicine powder (from the capsule K in the capsule accommodating chamber 5) through the inlet passage portion 18A toward the right-side and left-side outlet passage portions 18B, 18B. The air containing medicine powder in the right-side outlet passage portion 18B and the air containing medicine powder in the left-side outlet passage portion 18B are respectively directed to the right-side and left-side medicine powder passage 19, 19.

The right-side and left-side medicine powder passages 19, 19 are formed axially extending and respectively connected at their upper ends with right-side and left-side medicine powder spraying holes 20A, 20A. Each medicine powder passage 19 is straight and elongated so as to provide flow-regulating characteristics and straight advancing characteristics to the medicine powder passing through each medicine powder passage 19, so that the medicine powder is forcibly ejected from each spraying hole 20A. The spray holes 20A, 20A are respectively formed through right-side and left-side medicine powder spraying nozzle portions 20, 20, which project from the upper end surface of the upper section of the passage member 15. Each spraying nozzle portion 20 is generally frustoconical so as to be easily insertable into each of the nasal cavities of the patient. Each spray hole 20A is coaxial with the central part of the spraying nozzle portion 20 and extends axially to connect with the medicine powder passage 19, so that air containing medicine powder is ejected therethrough into each of the nasal cavities of the patient.

Here, as shown in FIG. 1, the right-side and leftside medicine powder spraying nozzle portions 20, 20 have respective centers or axes (no numerals) which are separated by a distance L1 ranging from 12 to 25 mm. As a result, the spraying nozzle portions 20, 20 can be fitted to nasal cavities of a wide range of patients from children having a relatively small distance (for example, 12 to 16 mm) between the nasal cavities to adults having a relatively large distance (for example, 16 to 22 mm) between the nasal cavities.

Figure 2:
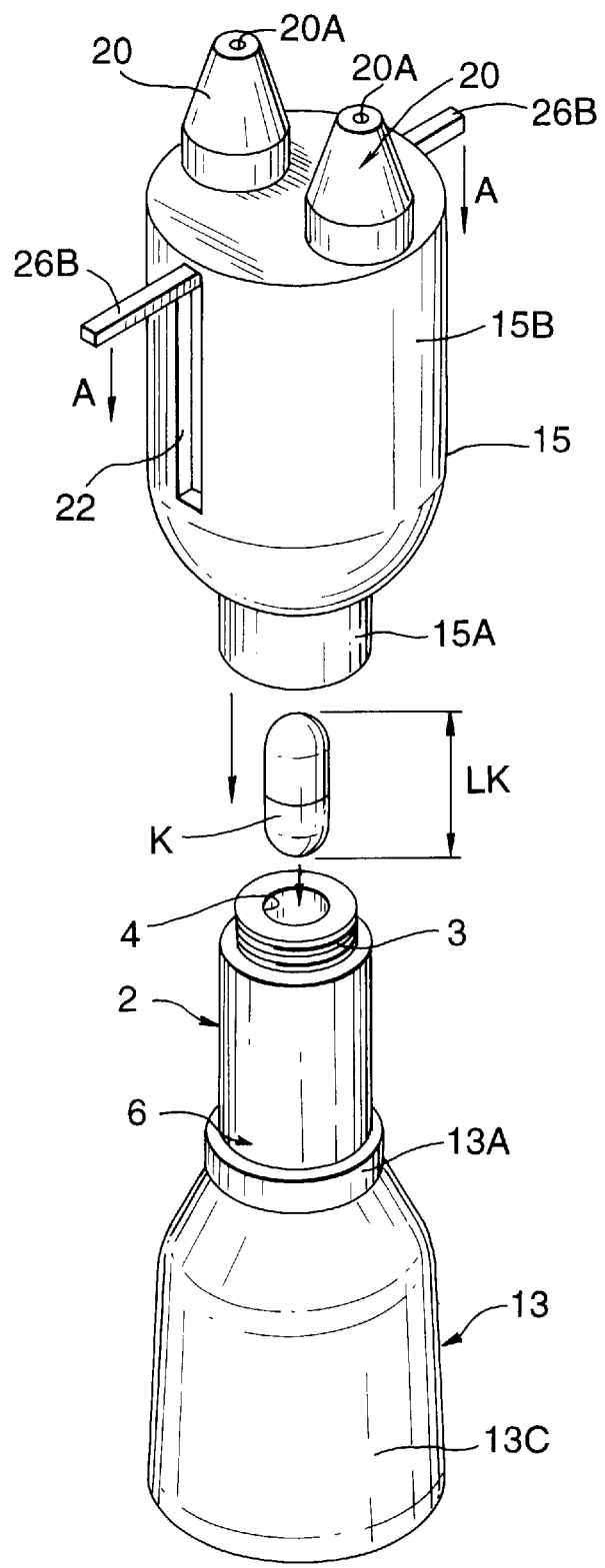
FIG. 2 is an exploded perspective view of the medicine administering device of FIG. 1.

The passage member 15 is formed with a perforator chamber 21 which is formed at the central part of the passage member 15 and extends axially to be located between the medicine powder passages 19, 19. As shown in FIG. 2, the passage member 15 is formed with a pair of elongate holes 22, 22 which are in communication with the perforator chamber 21 and open to the outer peripheral surface of the passage member 15. Each elongate hole 22 extends axially and is located symmetrical with respect to axis of the passage member 15. The passage member 15 is formed with a pin insertion hole 23 which connects the bottom part of the perforator chamber 21 and the branched passage section 18. A seal member 29 formed of rubber or plastic is securely fitted in a seal member installation depression (no numeral) formed in a part of the passage member 15 between the perforator chamber 21 and the branched passage section 18. The seal member 29 is located spaced from and facing the inlet passage portion 18A.

A perforator 25 is movably disposed inside the perforator chamber 21 and includes a pusher 26 which has a disc portion 26A slidably disposed in the perforator chamber 21. The disc portion 26A is provided with a pair of operation projections 26B, 26B which extend radially outwardly and are respectively located in the elongate holes 22, 22 of the passage member 15. A pin 27 is fixed at its upper or base end section to the disc portion 26A of the pusher 26 and extends axially to have a lower tip end section which is formed into a sharp needle 27A. Additionally, a return spring 28 is disposed in the perforator chamber 21 to return the pin 27 into its initial position at which the sharp needle 27A is located within the seal member 29.

Figure 3:
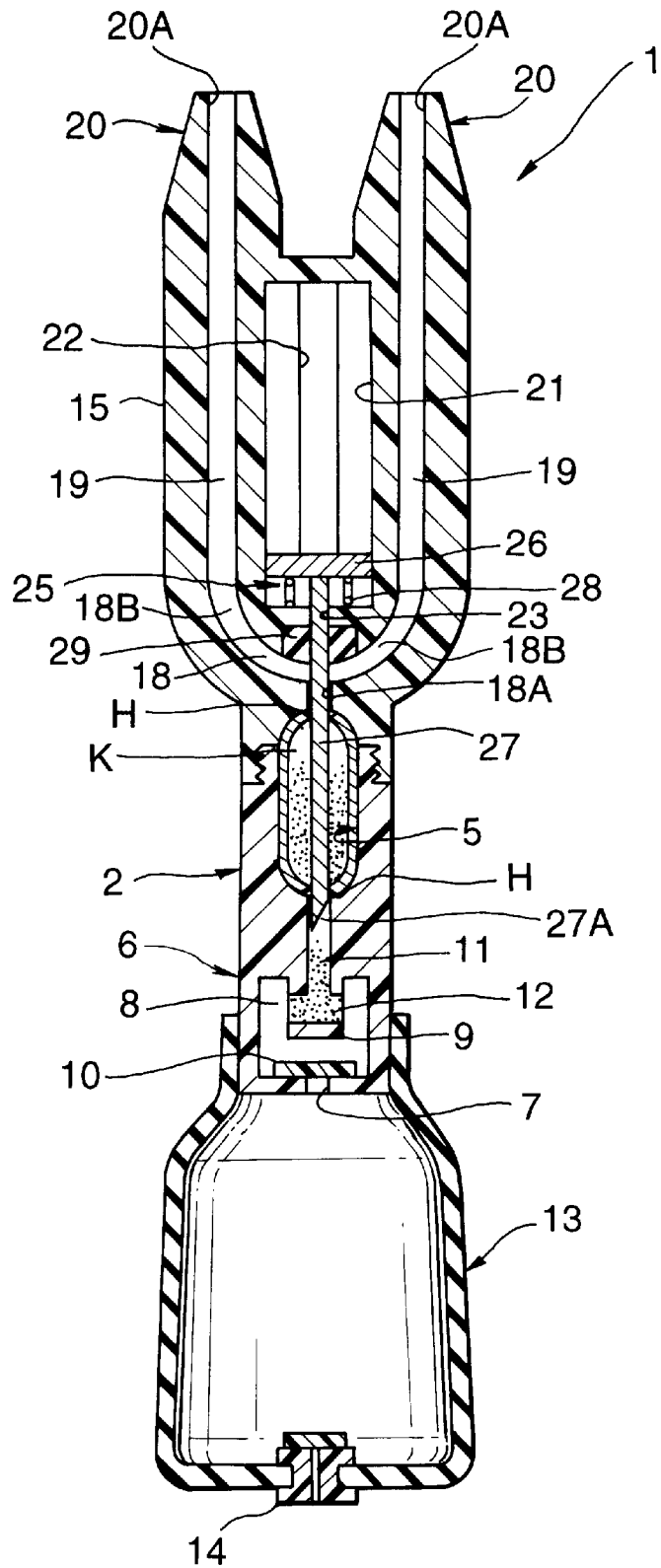
FIG. 3 is a vertical cross-sectional view similar to FIG. 1 but showing a second operational state of the medicine administering device of FIG. 1.

Here, as shown in FIG. 3, the perforator 25 is arranged as follows: When the respective operation projections 26B, 26B are shifted along the elongate holes 22 in the direction of arrows A in FIG. 2, the needle 27A is inserted axially into the capsule K in the capsule accommodating chamber 5, thereby forming the through-holes H, H in the capsule K. The seal member 29 is formed of an elastomeric material which is slidable relative to the pin 27 and maintains a sealing ability relative to medicine powder flowing through the branched passage section 18, thereby preventing medicine powder from penetrating into the perforator chamber 21.

Next, a manner of operation of the thus arranged first embodiment of the medicine administering device 1 for nasal cavities will be discussed.

First, the operation of perforating the capsule K will be explained.

The capsule K is loaded in the capsule hole lower part 4 of the capsule holder 2, and then the external thread 3 of the capsule holder 2 is engaged with the internal thread 16 of the passage member 15 so that the capsule K is accommodated inside the capsule accommodating chamber 5, including the capsule hole lower part 4 in the capsule holder and the capsule hole upper part 17 in the capsule holder 2 and the passage member 15.

Thereafter, the respective operation projections 26B, 26B of the pusher 26 are pressed down or moved in the direction of the arrows A in FIG. 2, so that the needle 27A of the pin 27 pierces the capsule K axially through the inlet passage portion 18A, thereby forming the through-holes H, H located at the axially opposite sides of the capsule K. At this time, the medicine powder in the capsule K may drop into the air supply passage 11 under the action of the needle 27A of the pin 27, in which the thus dropped medicine powder is trapped by the medicine powder receiving portion 12, thereby preventing medicine powder from adhering to and accumulating on the air supply valve member 10.

After such a perforation operation for the capsule K, the pusher 26 is automatically returned to its initial position under the action of the return spring 28, so that the passage portions 18A, 18B of the branched passage section 18 are brought into communication with the air supply passage 11 under a state where the through-holes H, H are formed at the axially opposite end sides of the capsule K.

Figure 4:
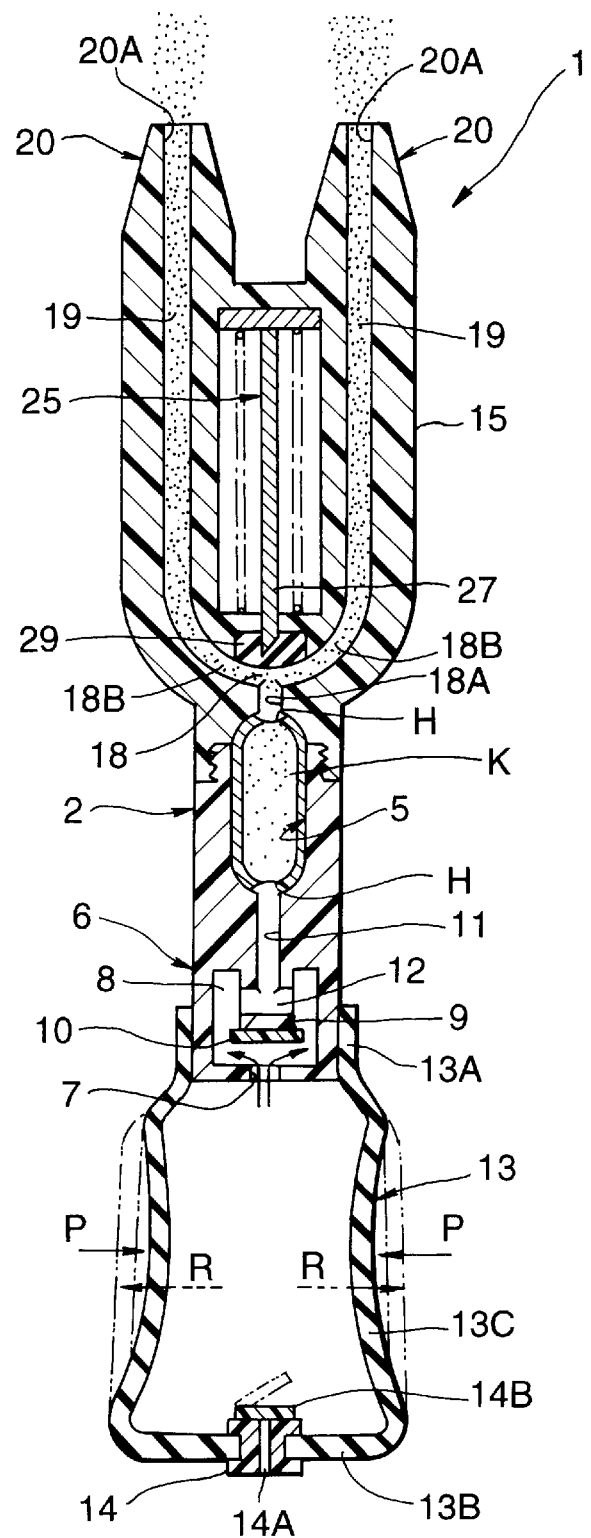
FIG. 4 is a vertical cross-sectional view similar to FIG. 1 but showing a third operational state of the medicine administering device of FIG. 1.

The operation of administering the medicine to the patient after the above perforation operation for the capsule K now will be explained with reference to FIG. 4.

First, the right-side and left-side medicine powder spraying nozzle portions 20, 20 are inserted respectively into the right-side and left-side nasal cavities of the patient. Then, the pressable portion 13C of the pump 13 is pressed in the directions of arrows P, P, so that air is supplied toward the capsule K accommodated in the capsule accommodating chamber 5 through the air supply passage 11 upon making a valve opening action of the air supply valve member 10 so as to open the air flow passage 7. Accordingly, the medicine powder in the capsule K is stirred and spread into air. As a result, the medicine powder is mixed with an air stream and flows through the branched passage section 18 into the right-side and left-side medicine powder passages 19, 19, and then is sprayed through the right-side and left-side spraying holes 20A, 20A into the nasal cavities of the patient.

After the above medicine administering operation, the pressable portion 13C of the pump 13 is moved in the directions of arrows R, R to be restored to its initial state. At this time, the air supply valve member 10 closes the air flow passage 7, while the valve member 14B opens the air suction passage 14A so that air is sucked from the outside into the pump 13 through the air suction passage 14A.

Thus, according to this embodiment of the medicine administering device 1, by setting the distance L1 between the spraying holes 20A, 20A of the right-side and left-side medicine powder spraying nozzle portions 20, 20 at a value ranging from 12 to 25 mm, the respective spraying holes 20A, 20A can be suitably positioned in the nasal cavities of a wide range of persons, from children having a small distance between the nasal cavities to adults having a large distance between the nasal cavities. As a result, medicine powder can be ejected to desired positions within the respective nasal cavities, thereby improving the effects of the medicine powder while extending a usable range of the medicine administering device 1.

It will be understood that a flow stream of air containing medicine powder from the capsule K is distributed through the branched passage section 18 into the right-side and left-side medicine powder passages 19, 19, so that medicine powder is administered simultaneously and in an equal amount into the right-side and left-side nasal cavities of the patient. As a result, the medicine powder inside the capsule can be administered to the patient by making pressing actions of the pump 13 about three times, without repeatedly inserting the medicine administering device into the respective right-side and left-side nasal cavities of the patient and undertaking many medicine administering operations for each nasal cavity, as required with conventional medicine administering devices. Thus, the medicine administering device 1 of this embodiment facilitates and simplifies a medicine administering operation, while shortening a time required for administering medicine.

Additionally, the inside volume (content volume) of the capsule K is set within the range from 0.1 to 1.4 cc. As a result, the medicine powder within the capsule K can be completely supplied to the patient without the remainder under the action of air stream flown into the capsule K during administration of the medicine, so that a predetermined amount of medicine powder is administered to the patient. This effectively improves the effects of the medicine and the reliability of the medicine administering device 1.

Further, the cross-sectional area of the air supply passage 11 is set within the range of 0.2 to 6.0 $mm^2$. As a result, air supplied from the pump 13 can be flown into the capsule K at suitable flow amount and speed, and therefore the air supply passage 11 is prevented from being clogged with medicine powder and the like while the medicine powder in the capsule K and air are mixed at a good ratio. Accordingly, medicine powder can be sprayed into the nasal cavities of the patient in a state to be effectively spread, thereby improving the effects of medicine powder to be administered to the patient.

Moreover, since the manually operated pump 13 is connected to the air supply section 6 to supply air into air supply section 6, an air stream can be easily formed by pressing the pressable portion 13C by the fingers of the patient, thus facilitating a medicine administering operation. Besides, the discharge amount of air from the pump 13 by each pressing action is set within the range of 10 to 60 cc, and therefore a suitable amount of air can be supplied through the air supply section 6 to the capsule K, thus improving the stirring efficiency of the medicine powder within the capsule K.

FIG. 5 illustrates a second embodiment of the medicine administering device 1' for nasal cavities, according to the present invention, which is similar to the first embodiment of the medicine administering device. The same reference numerals are assigned to the same parts and elements as those in the first embodiment so as to omit explanation of the same parts and elements for the purpose of simplicity of illustration. This embodiment has capsule accommodating chambers formed respectively in right-side and left-side medicine powder passages.

In this embodiment, the medicine administering device 1' for nasal cavities comprises the air supply section 6, which is formed with the air supply valve chamber 8, which in turn is communicable with the pump 13 through the air flow passage 7. The valve opening amount restricting portion 9 projects into the valve chamber 8 and is located facing the air flow passage 7. The air supply valve member 10 is located within the valve chamber 8 and is adapted to open or close the air flow passage 7. The air supply passage 11 is formed axially extending and communicated through the medicine powder receiving portion 12 with the valve chamber 8. The medicine powder receiving portion 12 is located upstream of the air supply passage 11 and adapted to trap medicine powder dropped through the air supply passage 11.

Here, the air supply passage 11 is connected at its upper end with a branched passage section 45 which will be discussed below. The air supply passage 11 has a cross-sectional area ranging from 0.2 to 6.0 mm$^2$, preferably 1.0 to 4.5 mm$^2$, like in the first embodiment of the medicine administering device 1. Air to be supplied from the pump 13 is flown into the capsule K at a suitable amount and at a suitable flow speed so as to mix medicine powder in the capsule K with air at a good mixing ratio.

The passage member 15 is disposed at the upper side of the air supply section 6 and includes a capsule holder 40, which is formed integral with the upper end of the air supply section 6. The capsule holder 40 is formed with right-side and left-side capsule hole lower parts 41, 41 which are separate from each other. The capsule holder lower parts 41, 41 are respectively to be combined with right-side and left-side capsule hole upper parts 44, 44 which will be discussed below, so as to form right-side and left-side capsule accommodating chambers 42, 42. Each capsule accommodating chamber 42 is adapted to store therein the capsule K and has a volume ranging from 0.1 to 1.4 cc, preferably 0.2 to 0.6 cc.

The passage member 15 includes a nozzle member 43 which is detachably fixed to the upper end of the capsule holder 40. The nozzle member 43 is formed at its upper end with the medicine powder spraying nozzle portions 20, 20. The nozzle member 43 is formed with the right-side and left-side capsule hole upper parts 44, 44 which open at the bottom face of the nozzle member 43.

The above-mentioned branched passage section 45 has right-side and left-side outlet passage portions 45A, 45A which are branched off from the upper end section of the air supply passage 11. Each outlet passage portion 45A extends obliquely upwardly and straight, so that the outlet passage portions 45A, 45A and the air supply passage 11 are arranged generally in a Y-shape. An angle a formed between the axes of the outlet passages 45A, 45A is within a range of 70 to 180 degrees, preferably 90 to 160 degrees, on a vertical plane containing the axis of the medicine administering device 1'. Air from the air supply passage 11 is generally equally distributed into the right-side and left-side medicine powder passages 19, 19, while the height of each outlet passage 45A is reduced, thereby small-sizing the medicine administering device 1'.

The right-side and left-side medicine powder passages 19, 19 are formed throughout the capsule holder 40 and the nozzle member 43. Each medicine powder passage 19 axially extends from the outlet passage 45A of the branched passage section 45 through the capsule accommodating chamber 2 to each of the right-side and left-side spraying holes 20A, 20A.

The right-side and left-side medicine powder spraying nozzle portions 20, 20 are generally frustoconical and project upward from the upper end face of the nozzle member 43. Each medicine powder spraying nozzle portion 20 is formed at its central part with the spraying hole 20A through which an air stream containing medicine powder is sprayed. Here, a distance L2 between the axes of the spraying holes 20A, 20A of the right-side and left-side spraying nozzle portions 20, 20 is set within a range of 12 to 25 mm. Accordingly, the spraying nozzle portions 20, 20 can be fitted to nasal cavities of a wide range of patients from children having a relatively small distance (for example, 12 to 16 mm) between the nasal cavities to adults having a relatively large distance (for example, 16 to 22 mm) between the nasal cavities.

A first perforator 48 is disposed movable relative to the capsule holder 40 and includes an operation ring 49, which is movably disposed on the outer peripheral surface of the air supply section 6. Two pins 50, 50 are fixed at its lower end or base section to the operation ring 49 and extend upwardly. The upper end section of each pin 50 is located to be insertable into the capsule accommodating chamber 42. The tip end of the upper end section of each pin 50 is formed into the shape of a sharp needle 50A. The first perforator 48 is adapted to form the through-holes at the axially opposite sides of the capsule K accommodated in each capsule accommodating chamber 42 by displacing the operation ring 49 of the first perforator 48.

Two seal members 51, 51 are respectively fixedly disposed near the upper ends of the outlet passage portions 45A, 45A of the branched passage section 45. Each seal member 51 is fitted within a depression (no numeral) formed in the capsule holder 40, and formed of an elastomeric material such as rubber or plastic. Each seal member 51 is adapted to maintain a powder-tight seal relative to the pin 50.

A second perforator 52 is provided separate from the passage member 15 and includes a grip section 53. A pin 54 is fixed at its upper end or base section to the grip section 53. The lower end section of the pin 54 is formed into the shape of a sharp needle 54A. The second perforator is adapted as follows: The pin 54 is inserted through the spraying hole 20A into the medicine powder passage 46 of each spraying nozzle portion 20 under a state where the grip section 53 is held with fingers of an operator or the patient, thereby forming the through-holes H, H at the axially opposite sides of the capsule K. It will be understood that the second perforator 52 may be omitted.

Next, a manner of operation of the second embodiment of the medicine administering device 1' will be discussed.

The capsules K, K are accommodated respectively in the right-side and left-side capsule accommodating chambers 42, 42. In this state, the operation ring 49 of the first perforator 48 is displaced upward or toward the nozzle member 43 so that the through-holes H, H are formed respectively at the axially opposite sides of each of the two capsules K, K.

The operation of administering the medicine to the patient after the above perforation operation for the capsule K now will be explained.

First, the right-side and left-side medicine powder spraying nozzle portions 20, 20 are inserted respectively into the right-side and left-side nasal cavities of the patient. Then, the pump 13 is pressed to supply air through air supply passage 11 and the branched passage section 45 to the capsules K, K accommodated respectively in the capsule accommodating chambers 42, 42, so that the medicine powder in the capsule K is stirred and spread into air. By this, the medicine powder in the capsule K is mixed into air so as to form an air stream containing medicine powder, and is supplied through the passage portions 45A, 45A of the branched passage section 45 into the right-side and left-side medicine powder passages 19, 19. Thus, the medicine powder is sprayed through the right-side and left-side spraying holes 20A, 20A of the medicine powder spraying nozzle portions 20, 20 into the right-side and left-side nasal cavities of the patient.

Also with this embodiment of the medicine administering device 1', generally the same effects as those in the first embodiment of the administering device 1 can be obtained. Additionally, according to this embodiment, the outlet passage portions 45A, 45A of the branched passage section 45 are arranged to have the angle α ranging from 70 to 180 degrees formed therebetween, and therefore air from the air supply passage 37 is generally equally distributed into the right-side and left-side medicine powder passages 19, 19, thereby supplying a generally equal amount of the medicine powder into each of the right-side and left-side nasal cavities of the patient. This improves a spraying efficiency of medicine powder and reliability of the medicine administering device for nasal cavities.

Figure 5:
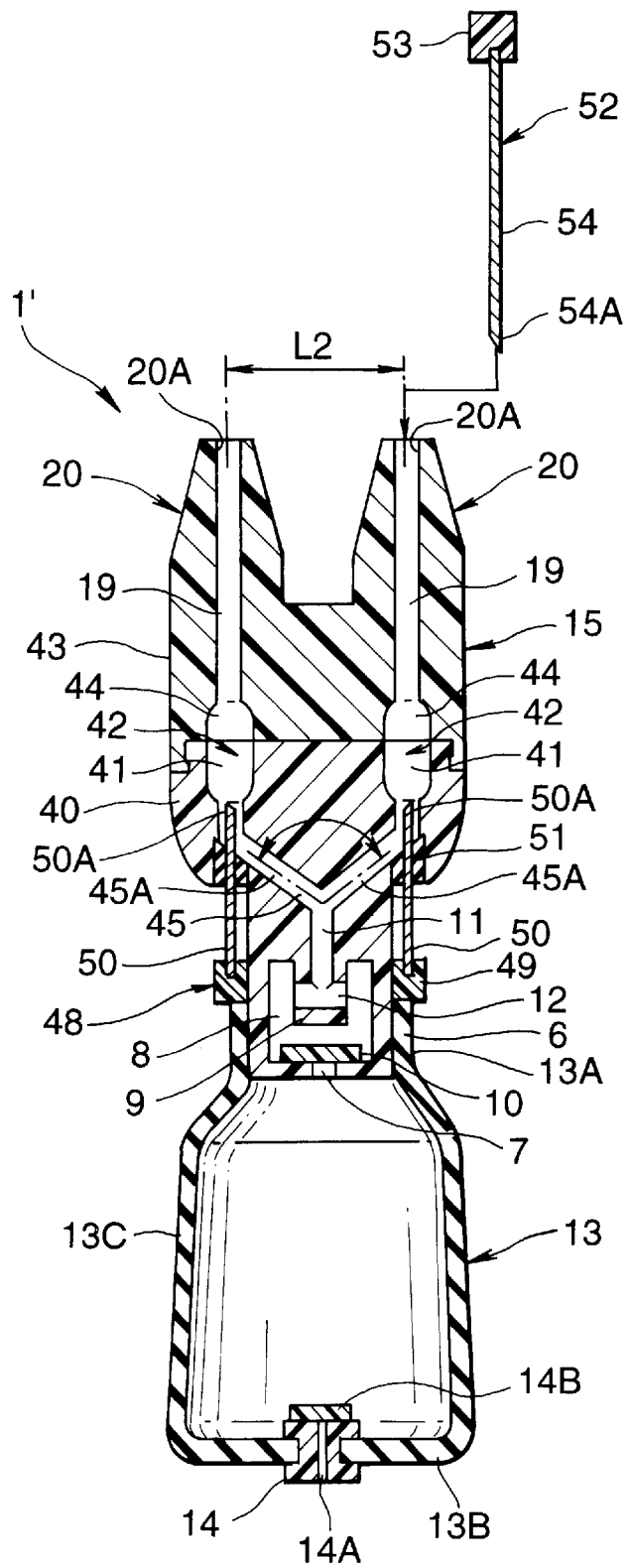
FIG. 5 is a vertical cross-sectional view of a second embodiment of the medicine administering device for nasal cavities, according to the present invention.

While the first and second embodiments of the medicine administering device 1, 1' have been shown and described such that the perforator 25, 48 is disposed in the passage member 15 and arranged to cause the pin 27, 50 to axially pierce the capsule K so as to form the through-holes H, H at the axially opposite sides of the capsule K, it will be appreciated that the through-holes H, H may be formed by using the perforator 52 shown in FIG. 5.

What is claimed is:

1. A medicine administering device for nasal cavities, comprising:

a capsule holding section having a capsule accommodating chamber for accommodating a capsule containing powder-state medicine;

an air supply section for supplying air toward the capsule held in said capsule holding section, said air supply section being connected to a first end of said capsule holding section and having an air supply passage which is in communication with said capsule accommodating chamber;

a branched passage section being connected to a second end of said capsule holding section, said branched passage section including an air flow passage in communication with said capsule accommodating chamber, said air flow passage being bifurcated to form first and second outlet passage portions, said air flow passage and said first and second outlet passage portions being arranged in a generally Y-shape;

a medicine passage section having first and second medicine passages through which air from said branched passage section flows to carry the medicine in the capsule into right-side and left-side nasal cavities of a patient, said first and second medicine passages being respectively in communication with the first and second outlet passage portions of said branched passage section;

a spraying section having first and second spraying holes which are respectively in communication with said first and second medicine passages, said first and second spraying holes respectively having first and second axes which are separate from each other by a distance ranging from 12 to 25 mm; and a perforator including a pin which is configured to be movable to form a through-hole in the capsule within said capsule holding section, said pin being insertable into said air flow passage and passable through said capsule accommodating chamber to form said through-hole which is to be in communication with said air supply passage of said air supply section.

2. A medicine administering device as claimed in claim 1, wherein said air flow passage and said air supply passage are generally coaxial with said capsule accommodating chamber.

3. A medicine administering device as claimed in claim 10, wherein said capsule accommodating chamber accommodates a capsule having a content volume ranging from 0.1 to 0.4 cc.

4. A medicine administering device as claimed in claim 10, wherein said air supply passage has a cross-sectional area ranging from 0.2 to 6.0 mm$^2$.

5. A medicine administering device as claimed in claim 10, further comprising a pump connected to said air supply section to supply air through said air supply section to the capsule.

6. A medicine administering device as claimed in claim 5, wherein said pump is manually operated and has an air discharge amount ranging from 10 to 60 cc.

7. A medicine administering device for nasal cavities, comprising:

a capsule holding section having a first capsule accommodating chamber for accommodating a first capsule containing powder-state medicine, and a second capsule accommodating chamber for accommodating a second capsule containing powder-state medicine;

a branched passage section connected to said capsule holding section, said branched passage section including an air flow passage in communication with said capsule accommodating chamber, said air flow passage being bifurcated to form first and second outlet passage portions, said air flow passage and said first and second outlet passage portions being arranged in a generally Y-shape, said first outlet passage portion being connected to a first end of said first capsule accommodating chamber, said second outlet passage portion being connected to a first end of said second capsule accommodating chamber;

an air supply section for supplying air through said branched passage section toward said capsule holding section, said air supply section having an air supply passage which is in communication with said air flow passage of said branched passage section;

a medicine passage section having first and second medicine passages through which air from said branched passage section flows, said first medicine passage being in communication with a second end of said first capsule accommodating chamber and said second medicine passage being in communication with a second end of said second capsule accommodating chamber;

a spraying section having first and second spraying holes that are in communication with said first and second medicine passages, respectively, said first and second spraying holes having first and second axes, respectively, that are separated from each other by a distance ranging from 12 to 25 mm; and a perforator including first and second pins that are connected to each other, said first pin being passable through said first capsule accommodating chamber to form the through-hole in the first capsule, said second pin being passable through said second capsule accommodating chamber to form the through-hole in the second capsule.

8. A medicine administering device as claimed in claim 7, wherein said first medicine passage and said first capsule accommodating chamber are coaxial, and said second medicine passage and said second capsule accommodating chamber are coaxial.

9. A medicine administering device for nasal cavities, comprising:

a medicine passage section including first and second medicine passages for communication with right-side and left-side nasal cavities of a patient;

a capsule holding section including first and second capsule accommodating chambers for accommodating respectively first and second capsules of powder-state medicine, said first and second capsule accommodating chambers being respectively in communication with said first and second medicine passages so that the medicine in the first capsule and the medicine in the second capsule is supplied respectively into said first and second medicine passages;

an air supply section including an air supply passage through which air to be supplied flows;

a branched passage section disposed between said first and second capsule accommodating chambers and said air supply section, said branched passage section including an air flow passage that bifurcates to form first and second outlet passage portions which are respectively in communication with said first and second capsule accommodating chambers, said air flow passage and said first and second outlet passage portions formed in a generally Y-shape;

a spraying section including first and second spraying holes which are respectively in communication with said first and second medicine passages, said first and second spraying holes respectively having first and second axes which are separate from each other by a distance ranging from 12 to 25 mm; and a perforator including first and second pins configured to be movable relative to said capsule holding section, said first pin being passable through said first capsule accommodating chamber to form the through-hole in the first capsule, said second pin being passable through said second capsule accommodating chamber to form the through-hole in the second capsule.

* * * * *